(12) United States Patent
Imamura et al.

(10) Patent No.: US 7,589,060 B2
(45) Date of Patent: Sep. 15, 2009

(54) THERAPEUTIC AGENT FOR HAIR-RELATED PROBLEMS AND METHOD FOR SCREENING FOR THE SAME

(75) Inventors: Toru Imamura, Ibaraki (JP); Mitsuko Kawano, Ibaraki (JP); Akiko Kuramochi, Ibaraki (JP); Masashi Suzuki, Ibaraki (JP); Masahiro Asada, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/662,897

(22) PCT Filed: Sep. 8, 2005

(86) PCT No.: PCT/JP2005/016535

§ 371 (c)(1),
(2), (4) Date: Mar. 15, 2007

(87) PCT Pub. No.: WO2006/030693

PCT Pub. Date: Mar. 23, 2006

(65) Prior Publication Data

US 2008/0139469 A1 Jun. 12, 2008

(30) Foreign Application Priority Data

Sep. 15, 2004 (JP) ............................. 2004-268242

(51) Int. Cl.
*C07K 14/50* (2006.01)
*A61K 38/18* (2006.01)
(52) U.S. Cl. .......................................... 514/2; 530/399
(58) Field of Classification Search ...................... None
See application file for complete search history.

(56) References Cited

U.S. PATENT DOCUMENTS

2003/0170822 A1    9/2003    Itoh

FOREIGN PATENT DOCUMENTS

| JP | 4-224522 A | 8/1992 |
|----|------------|--------|
| JP | 5-43424 A  | 2/1993 |
| JP | 9-316096 A | 12/1997 |

OTHER PUBLICATIONS

Ohbayashi et al. J. Biol. Chem. 273(29): 18161-18164, 1998.*
Hu et al. Oncogene 18: 2635-2642, 1999.*
Shimoaka et al. J. Biol. Chem. 277(9): 7493-7500, 2002.*
Cedric Blanpain, et al, "Self-Renewal, Multipotency, and the Existence of Two Cell Populations Within an Epithelial Stem Cell Niche", Cell, vol. 118, No. 5, Sep. 3, 2004, pp. 635-648.

* cited by examiner

*Primary Examiner*—Christine J Saoud
(74) *Attorney, Agent, or Firm*—Sughrue Mion, PLLC

(57) ABSTRACT

It is intended to elucidate the effect of promoting hair follicle growth and to provide the following therapeutic agents for hair-related problems (1) to (3):
(1) a hair growth promoting agent, comprising as an active ingredient an expression vector incorporating a full-length FGF-18, a partial peptide thereof, or a cDNA encoding the full-length FGF-18 or the partial peptide;
(2) a hair regrowth promoting agent, comprising as an active ingredient an expression vector incorporating a full-length FGF-18, a partial peptide thereof, or a cDNA encoding the full-length FGF-18 or the partial peptide; and
(3) a therapeutic agent for alopecia, comprising as an active ingredient an expression vector incorporating a full-length FGF-18, a partial peptide thereof, or a cDNA encoding the full-length FGF-18 or the partial peptide.

2 Claims, 6 Drawing Sheets

A DPC

B ORSC

C DF

D EK

THERAPEUTIC AGENT FOR HAIR-RELATED PROBLEMS AND METHOD FOR SCREENING FOR THE SAME

TECHNICAL FIELD

The present invention relates to a therapeutic agent for hair-related problems, which comprises an ingredient promoting hair follicle (a synonym for hair bulb) growth and is used as a hair growth promoting agent, a hair regrowth promoting agent, or a therapeutic agent for alopecia, and a screening method for each thereof.

BACKGROUND ART

A variety of polypeptide growth factors, including fibroblast growth factors (hereinafter, referred to as FGFs), are known to be expressed in skin tissue. In both mice and humans, FGFs are encoded by twenty-two distinct genes (Ornitz D M, Itoh N: Fibroblast growth factors, Genome Biol. 2: REVIEWS 3005, 2001). Particularly, FGF-1, FGF-2, FGF-5, FGF-7, FGF-10, FGF-13, and FGF-22 are expressed in skin cells and hair follicular cells and control hair growth and skin regeneration (as reported in the following non-patent documents: du Cros D L: Fibroblast growth factor and epidermal growth factor in hair development, J. Invest. Dermatol. 101: 106S-113S. 1993; du Cros D L, Isaacs K, Moore G P: Distribution of acidic and basic fibroblast growth factors in ovine skin during follicle morphogenesis, J. Cell Sci. 105: 667-674, 1993; Hebert J M, Rosenquist T, Gotz J, Martin G R: FGF5 as a regulator of the hair growth cycle: Evidence from targeted and spontaneous mutations, Cell 78: 1017-1025, 1994; Danilenko D M, Ring B D, Yanagihara D, Benson W, Wiemann B, Starnes C O, Pierce G F: Keratinocyte growth factor is an important endogenous mediator of hair follicle growth, development, and differentiation, American J. Pathol. 147: 145-154, 1995; Marchese C, Chedid M, Dirsch O R, et al: Modulation of keratinocyte growth factor and its receptor in reepithelializing human skin, J. Exp. Med. 182: 1369-1376, 1995; Guo L, Degenstein L, Fuchs E: Keratinocyte growth factor is required for hair development but not for wound healing, Genes Dev. 10: 165-175, 1996; Rosenquist T A, Martin G R: Fibroblast growth factor signaling in the hair growth cycle: Expression of the fibroblast growth factor receptor and ligand genes in the murine hair follicle, Developmental Dynamics 205: 379-386, 1996; Petho-Schramm A, Muller H J, Paus R: FGF5 and the murine hair cycle. Arch. Dermatol. Res. 288: 264-266, 1996; Mitsui S, Ohuchi A, Hotta M, Tsuboi R, Ogawa H: Genes for a range of growth factors and cyclin-dependent kinase inhibitors are expressed by isolated human hair follicles, Br. J. Dermatol. 137: 693-698, 1997; Ortega S, Ittmann M, Tsang S H, Ehrlich M, Basilico C: Neuronal defects and delayed wound healing in mice lacking fibroblast growth factor-2, Proc. Natl. Acad. Sci. U.S.A. 95: 5672-5677, 1998; Suzuki S, Kato T, Takimoto H, et al: Localization of rat FGF-5 protein in skin macrophage-like cells and FGF-5S protein in hair follicle: Possible involvement of two Fgf-5 gene products in hair growth cycle regulation, J. Invest. Dermatol. 111: 963-972, 1998; Suzuki S, Ota Y, Ozawa K, Imamura T: Dual-mode regulation of hair growth cycle by two Fgf-5 gene products, J. Invest. Dermatol. 114: 456-463, 2000; Nakatake Y, Hoshikawa M, Asaki T, Kassai Y, Itoh N: Identification of a novel fibroblast growth factor, FGF-22, preferentially expressed in the inner root sheath of the hair follicle, Biochem. Biophys. Acta. 1517: 460-463, 2001; Stenn K S, Paus R: Controls of hair follicle cycling, Physiol. Rev. 81: 449-494, 2001; Beyer T A, Werner S, Dickson C, Grose R: Fibroblast growth factor 22 and its potential role during skin development and repair, Exp. Cell Res. 287: 228-236, 2003; and Kawano M, Suzuki S, Suzuki M, Oki J, Imamura T: Bulge- and basal layer-specific expression of fibroblast growth factor 13 (FHF-2) in mouse skin, J. Invest. Dermatol. 122: 1084-1090, 2004).

Furthermore, JP Patent Publication (Kokai) No. 4-224522 A (1992) discloses a method for promoting hair growth and a method for treating baldness through the use of FGF-5. However, as disclosed in Suzuki S, Ota Y, Ozawa K, Imamura T: Dual-mode regulation of hair growth cycle by two Fgf-5 gene products, J. Invest. Dermatol. 114: 456-463, 2000, FGF-5 gene products are known to have a function of inducing catagen with regard to hair follicular cells. Hence, it is unrealistic to promote hair growth or treat baldness through the use of FGF-5 as disclosed in JP Patent Publication (Kokai) No. 4-224522 A (1992). In addition, detailed examination of the description of such patent document has revealed that such document fails to demonstrate that FGF-5 exerts the effect of promoting hair growth.

Documents including the above non-patent documents suggest the important role of FGFs in skin cell growth and differentiation. However, how FGF family members are involved in the effect of promoting hair follicle growth and the effects of promoting hair growth and hair regrowth following the thus promoted hair follicle growth remains unknown.

DISCLOSURE OF THE INVENTION

Objects to be Achieved by the Invention

The present invention has the objects of elucidating the effect of promoting hair follicle growth and providing a therapeutic agent for hair-related problems, which is used as a novel hair growth promoting agent, a hair regrowth promoting agent, and an agent for treating alopecia.

Means to Solve the Problems

To achieve the above objects, the present inventors have extensively investigated expression of all 22 genes belonging to the FGF family at each stage (telogen, anagen, and catagen) of the hair growth cycle in order to specify FGF genes that play important roles in the growth of hair and hair follicles. As a result, the present inventors have discovered a high expression level of an FGF-18 gene, the functions in skin of which has been unknown. Furthermore, the present inventors have conducted detailed functional analysis concerning FGF-18, discovering that FGF-18 has a function of promoting the growth of hair papilla cells, which are thought to control hair follicle growth. Based on such novel findings, the present inventors first assumed that FGF-18 promotes hair growth and then experimentally confirmed the promotion. Hence, the present inventors have completed the present invention.

Specifically, the present invention encompasses the following (1) to (3):

(1) a hair growth promoting agent, comprising as an active ingredient an expression vector incorporating a full-length FGF-18, a partial peptide thereof, or a cDNA encoding the full-length FGF-18 or the partial peptide;

(2) a hair regrowth promoting agent, comprising as an active ingredient an expression vector incorporating a full-length FGF-18, a partial peptide thereof, or a cDNA encoding the full-length FGF-18 or the partial peptide; and (3) a therapeutic agent for alopecia, comprising as an active ingredient an expression vector incorporating a full-length FGF-18, a partial peptide thereof, or a cDNA encoding the full-length FGF-18 or the partial peptide.

The above agents (1) to (3) may further comprise other protein growth factors and/or hair-growth promoting agents.

Examples of other protein growth factors include epidermal growth factors, platelet-derived growth factors, factors belonging to the FGF family other than FGF-18, transforming growth factor-α, transforming growth factor-β, factors belonging to a transforming growth factor-β superfamily, insulin-like growth factor-I, and insulin-like growth factor-II. The above agents (1) to (3) may comprise one type of such "other protein growth factors" or may comprise a plurality of such types. However, examples of such agents are not limited to these examples.

Examples of a hair growth promoting agent include, but are not limited to, minoxidil, minoxidil analogs, minoxidil derivatives, anti-androgen, 5α-reductase inhibitors, and Finasteride (Propecia). The above agents (1) to (3) may comprise one type or a plurality of such types of hair growth promoting agents.

Furthermore, the present invention encompasses the following (4) to (6):

(4) a screening method, comprising steps of causing a test substance to come into contact with a cultured animal cell or an experimental animal and monitoring the expression of an FGF-18 gene in the cultured animal cell or the experimental animal and using as a candidate for a hair growth agent a test substance having a function of promoting the expression of the FGF-18 gene;

(5) a screening method, comprising steps of causing a test substance to come into contact with a cultured animal cell or an experimental animal and monitoring the expression of an FGF-18 gene in the cultured animal cell or the experimental animal and using as a candidate for a hair regrowth promoting agent a test substance having a function of promoting the expression of the FGF-18 gene; and (6) a screening method, comprising steps of causing a test substance to come into contact with a cultured animal cell or an experimental animal and monitoring the expression of an FGF-18 gene in the cultured animal cell or the experimental animal and using as a candidate for a therapeutic agent for alopecia a test substance having a function of promoting the expression of the FGF-18 gene.

Effect of the Invention

According to the present invention, a therapeutic agent for hair-related problems can be provided that can be used as a hair growth promoting agent, a hair regrowth promoting agent, and a therapeutic agent for alopecia, such therapeutic agent exerting its effects through promotion of hair follicle growth. Through the use of the hair growth promoting agent, the hair regrowth promoting agent, and the therapeutic agent for alopecia according to the present invention, promotion of hair growth and hair regrowth in the cases of baldness and thinning hair and treatment of alopecia can be more effectively achieved.

Furthermore, by the use of the screening method according to the present invention, substances effective as therapeutic agents for hair-related problems such as a hair growth agent, a hair regrowth promoting agent, and a therapeutic agent for alopecia can be screened for.

BEST MODE OF CARRYING OUT THE INVENTION

Figure 1A:
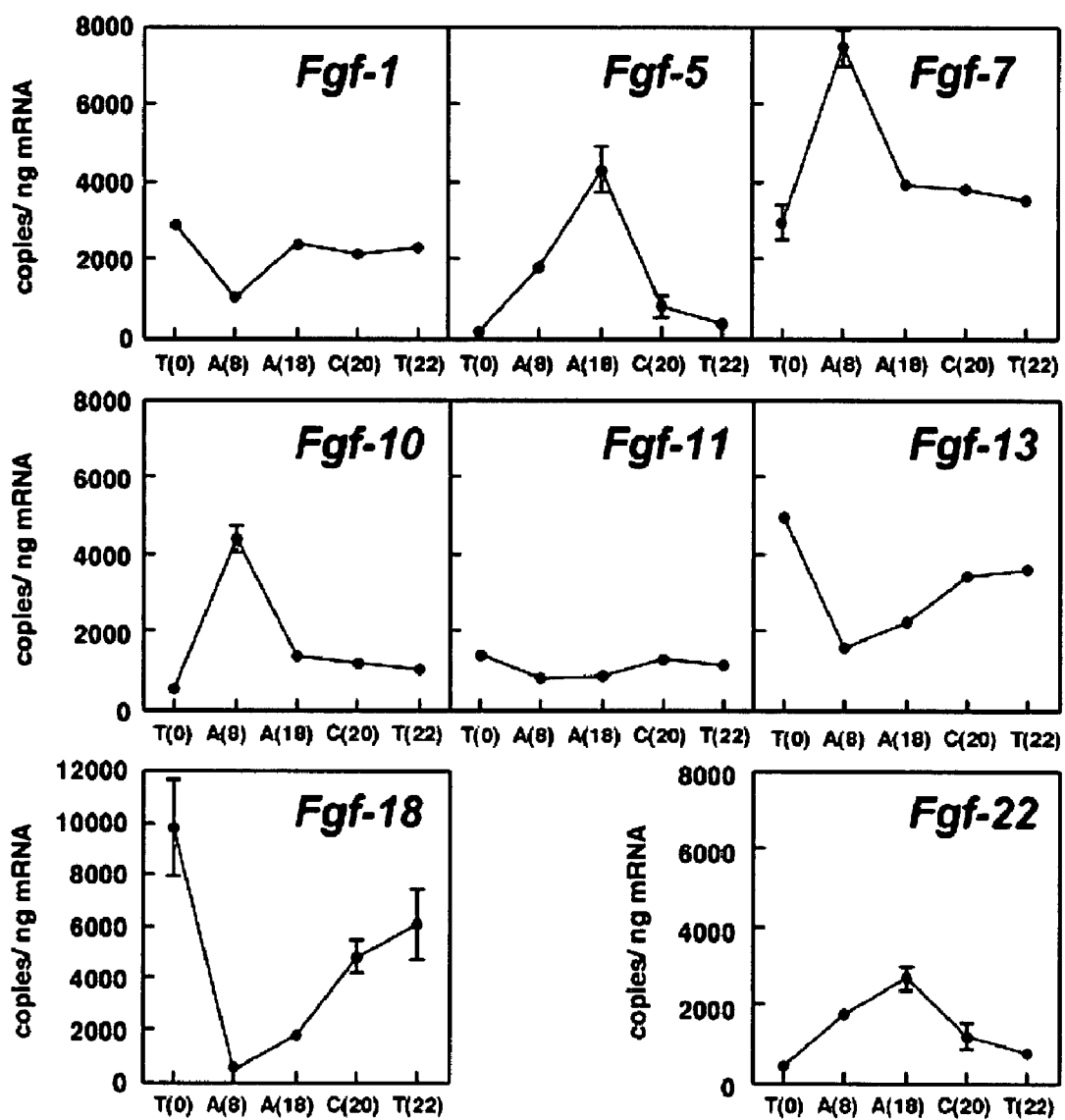
FIG. 1A shows characteristic graphs showing the expression profiles of FGF-1, -5, -7, -10, -11, -13, -18, and -22 genes during each hair cycle.

Hereinafter, the present invention will be described in detail.

Through application of the present invention, a therapeutic agent for hair-related problems can be provided that can be used as a novel hair growth promoting agent, hair regrowth promoting agent, and therapeutic agent for alopecia. Factors common to these agents are containment of a full-length FGF-18 or a partial peptide thereof and possession of the effect of promoting hair follicle (which may also be referred to as hair bulb) growth.

Hair follicles are apparatuses for hair development. The hair follicle growth cycle is composed of anagen, catagen, and telogen (following catagen), where telogen is followed by anagen. Generally in a mouse experimental system, anagen lasts 1 to 19 days after depilation and catagen lasts 20 to 21 days after depilation. Moreover, it is known that telogen is initiated on day 21 to 22 after depilation. During anagen, new hair growth (elongation) is activated and hair follicle growth is activated within the skin, so that the bottom thereof reaches near the lower portion of the skin tissue. In contrast, during telogen, hair follicles of small sizes are present near the skin surface. Furthermore, the skin thickness during anagen is completely different from that during telogen. Furthermore, in early anagen, melanin pigments are synthesized, so that bluish skin can be visually confirmed. Accordingly, the progress of the hair follicle growth cycle can be evaluated based on such bluish skin observed from the outside of the skin. Furthermore, when an incision is made in the skin during anagen and then the skin is observed from the other side, hair follicles abundantly containing melanin pigments are seen arrayed at high densities, such that the darkened reverse side of the skin can be visually confirmed. In contrast, during telogen, it can be visually confirmed that the reverse side of the skin remains white. For example, in a mouse experimental system, all hairs on the back of a 7- to 8-week-old mouse are in telogen. Furthermore, anagen is initiated along with depilation of hair growing on the skin of such a mouse.

1. FGF-18

As FGF-18 contained in the novel hair growth promoting agent, the novel hair regrowth promoting agent, and the novel therapeutic agent for alopecia according to the present invention, human-derived FGF-18 comprising the amino acid sequence shown in SEQ ID NO: 2 can be used, for example. Examples of FGF-18 that can be used herein are not limited to those derived from humans and include FGF-18 derived from other mammals. Examples of such other mammals include, but are not limited to, mice, rats, chickens, turkeys, cattle, pigs, sheep, and rabbits. For example, a gene encoding FGF-18 can be isolated according to a standard method from a non-human mammal with the use of a probe prepared based on the nucleotide sequence (shown in SEQ ID NO: 1) of human-derived FGF-18.

The nucleotide sequence and the amino acid sequence of such human-derived FGF-18 are shown in SEQ ID NOS: 1 and 2, respectively. The amino acid sequence of mouse-derived FGF-18 is shown in SEQ ID NO: 3. The amino acid sequence of rat-derived FGF-18 is shown in SEQ ID NO: 4. The amino acid sequence of chicken-derived FGF-18 is shown in SEQ ID NO: 5. As understood from comparison of these amino acid sequences shown in SEQ ID NOS: 2, 3, 4, and 5, mammals share very high homology in terms of FGF-18, and FGF-18 functions are almost the same in all mammals.

In addition, a protein that comprises an amino acid sequence derived from the amino acid sequence shown in SEQ ID NO: 2, 3, 4, or 5 by deletion, substitution, and/or addition of 1 or several amino acids and has the effect of promoting hair follicle growth is also included among the examples of FGF-18 according to the present application. The term "several amino acids" used herein means 2 to 54 amino acids and more preferably 2 to 27 amino acids, for example.

The region between the $55^{th}$ and the $177^{th}$ amino acids in the amino acid sequence shown in SEQ ID NO: 2 is thought to be a core portion common to various FGFs. Therefore, a portion derived from the amino acid sequence shown in SEQ ID NO: 2 by deletion, substitution, and/or addition can be used as FGF-18 in the present application without losing the effect of promoting hair follicle growth as long as all such deletions, substitutions, and/or additions of 1 or several amino acids have taken place in regions other than the region (core portion) between the $55^{th}$ and the $177^{th}$ amino acids in the amino acid sequence shown in SEQ ID NO: 2.

Furthermore, the novel hair growth promoting agent, the novel hair regrowth promoting agent, and the novel therapeutic agent for alopecia according to the present invention may be partial fragments of the above examples of FGF-18. An example of such a partial FGF-18 fragment is a polypeptide comprising the amino acid sequence between the $55^{th}$ and the $177^{th}$ amino acids shown in SEQ ID NO: 2. Specifically, even when such polypeptide comprises such amino acid sequence between such $55^{th}$ and the $177^{th}$ amino acids, it is highly probable that such polypeptide would bind to a receptor and heparin and has the effect of promoting hair follicle growth. Furthermore, a polypeptide comprising the amino acid sequence between the $28^{th}$ and the $207^{th}$ amino acids can most preferably be used as a partial FGF-18 fragment. In addition, even a polypeptide comprising an amino acid sequence corresponding to the above range in the amino acid sequence shown in SEQ ID NO: 3, 4, or 5 can be used as an active ingredient of the novel hair growth promoting agent, the novel hair regrowth promoting agent, and the novel therapeutic agent for alopecia according to the present invention. Furthermore, a partial FGF-18 fragment may be a peptide with a length of approximately 3 to 50 amino acids that corresponds to the portion of the amino acid sequence between the $1^{st}$ and the $207^{th}$ amino acids, as long as such fragment is required for exertion of FGF-18 activity in the present invention. However, even a peptide comprising amino acids and having a length that exceeds the range of the above numerical values is also included among examples of the partial FGF-18 fragments according to the present invention.

The full-length FGF-18 and partial peptides thereof as defined above have the effect of promoting hair follicle growth. Such effect can be confirmed, as described in detail in the following Examples, by culturing hair follicles in media containing full-length FGF-18 and partial peptides thereof and examining the ability of the full-length FGF-18 and that of the partial peptides to induce DNA synthesis in hair papilla cells, dermal fibroblasts, and epidermal keratinocytes with the use of a pure culture system or a composite culture system in combination with outer root sheath cells corresponding to each such cell type. Moreover, the effect of promoting hair follicle growth of full-length FGF-18 and of partial FGF-18 peptides can be confirmed by subcutaneously administering full-length FGF-18 and partial peptides thereof to experimental animals experiencing the telogen stage of the hair cycle and then observing the resulting hair follicle growth.

2. Hair Growth Promoting Agent, Hair Regrowth Promoting Agent, and Therapeutic Agent for Alopecia The full-length FGF-18 polypeptide and/or the partial polypeptides thereof as described in "1. FGF-18" above are formulated into optimal forms for application to the skin, such as solutions, creams, ointments, gel, lotions, shampoos, or aerosol preparations and then provided as the forms of the hair growth promoting agent, the hair regrowth promoting agent, and the therapeutic agent for alopecia.

In particular, the hair growth promoting agent, the hair regrowth promoting agent, and the therapeutic agent for alopecia are administered in the forms of pharmaceutical compositions containing FGF-18 together with pharmacologically acceptable carriers optimized for localized administration. The hair growth promoting agent, the hair regrowth promoting agent, and the therapeutic agent for alopecia each further preferably contain heparin. Such FGF-18-comprising hair growth promoting agent, hair regrowth promoting agent, and therapeutic agent for alopecia each generally contain an active compound at a concentration ranging from approximately 0.01 to approximately 100 μg/day/cm$^2$ and preferably ranging from approximately 0.1 to approximately 10 μg/day/cm$^2$ in a pharmaceutically acceptable carrier. In other words, FGF-18 concentration is a concentration of such active compound generally ranging from approximately 0.01 to approximately 100 μg/day/cm$^2$ and preferably ranging from approximately 0.1 to approximately 10 μg/day/cm$^2$ in a pharmaceutically acceptable carrier.

Furthermore, the hair growth promoting agent, the hair regrowth promoting agent, and the therapeutic agent for alopecia may also comprise other purified protein growth factors (PGFs) or recombinant-derived PGFs known in the art. Examples of growth factors for increasing or enhancing the effect of FGF-18 of promoting hair follicle growth are not particularly limited and include a group of growth factors such as an epidermal growth factor (EGF), a platelet-derived growth factor (PDGF), a transforming growth factor-α (TGF-α), a transforming growth factor-β (TGF-β), an insulin-like growth factor (IGF), and vascular endothelial cell growth factor (Van Brunt and Klausner, Biotechnology, vol. 6, pp. 25-30, 1988).

EGF, hEGF, and the methods of producing the same are disclosed in the following references: U.S. Pat. No. 3,914,824, U.S. Pat. No. 3,948,875, U.S. Pat. No. 4,528,186, PCT Patent Publication No. WO/85/00369, and Proceedings of National Academy of Science U.S.A. vol. 80, pp. 7461-7465 (1983).

PDGF, hPDGF, and the methods for producing the same are disclosed in the following references: U.S. Pat. No. 4,350,687; Nature, vol. 320, pp. 695-699 (1986); EMBO Journal vol. 3, pp. 921-928 (1984); and EMBO Journal, vol. 3, pp. 2963-2967 (1984).

TGF-α, hTGF-α, and the methods for producing the same are disclosed in the following references: EP Patent Publication No. 154,434 and Cell, vol. 38, pp. 287-297 (1984). TGF-β, hTGF-β, and the methods for producing them are disclosed in the following references: U.S. Pat. No. 4,774,228; U.S. Pat.

No. 4,774,322; DNA, vol. 7, pp. 1-8 (1988); and Journal of Biological Chemistry, vol. 262, pp. 12127-12131 (1987).

IGF-I, hIGF-I, and the methods for producing the same are disclosed in the following references: PCT Patent Publication No. WO/88/03409, EP Patent Publication No. 264,074, and EP Patent Publication No. 219,814. IGF-II, hIGF-II, and the methods for producing the same are disclosed in the following reference: EP patent Publication No. 280,460.

Moreover, the hair growth promoting agent, the hair regrowth promoting agent, and the therapeutic agent for alopecia may also comprise other compounds or drugs known in the art showing activity to promote hair growth. Examples of other hair growth promoting agents are not particularly limited and include anti-androgen, a 5α-reductase inhibitor, minoxidil, a minoxidil derivative or an analog thereof, and compounds associated with these examples or analogs of such compounds.

Furthermore, examples of pharmacologically acceptable carriers optimized for localized administration include, but are not particularly limited to, ointments such as hydrophilic petrolatum and a polyethylene glycol ointment, pastes of a rubber such as xanthan rubber, alcohol, solutions such as aqueous solutions and buffers, gels such as aluminum hydroxide gel and sodium alginate gel, albumins such as a human or animal albumin, collagens such as human or animal collagen, cellulose such as alkylcellulose, hydroxyalkylcellulose, and alkylhydroxyalkylcellulose, methylcellulose, hydroxyethylcellulose, carboxymethylcellulose, hydroxypropylmethylcellulose, and hydroxypropylcellulose, polymers such as Pluronic (Trademark) polyol as exemplified by Pluronic (trademark) F-127, tetronics such as tetronic 1508, and alginates such as sodium alginate.

The hair growth promoting agent, the hair regrowth promoting agent, and the therapeutic agent for alopecia according to the present invention may also comprise as an active ingredient an expression vector having cDNA encoding the full-length FGF-18 polypeptide and/or the partial polypeptides thereof as explained in "1. FGF-18" above. Specifically, the hair growth promoting agent, the hair regrowth promoting agent, and the therapeutic agent for alopecia according to the present invention can be used for gene therapy using the above expression vector. Such expression vector is provided with a promoter sequence or the like for realization of expression in animal cells. However, such sequence is not particularly limited to this example. A plasmid vector, viral vector, or the like can be used as an expression vector, but examples of such expression vector are not limited thereto.

More specifically, in the above gene therapy, cDNA encoding a full-length FGF-18 polypeptide and/or a partial polypeptide thereof (as explained in "1. FGF-18" above) is incorporated into a viral vector, for example. Patients are infected with viruses (detoxified) having the recombinant viral vector. The full-length FGF-18 polypeptide and/or the partial polypeptide thereof is produced in a patient's body, so that hair follicle growth can be promoted.

As a method for introducing such hair growth promoting agent, hair regrowth promoting agent, and therapeutic agent for alopecia for gene therapy into cells, a gene transfer method using a viral vector and a non-viral gene transfer method (Nikkei Science, April 1994, pp. 20-45; Extra Edition of Experimental Medicine, 12 (15) (1994); Separate Volume of Experimental Medicine, "Basic Techniques for Gene Therapy (Idenshi chiryo no kisogijutsu))," YODOSHA (1996)) can both be applied herein.

Examples of gene transfer methods using viral vectors include methods that involve incorporating DNA that encodes TR4 or mutant TR4 into a DNA virus or an RNA virus such as a retrovirus, adenovirus, adeno-associated virus, herpes virus, vaccinia virus, poxvirus, poliovirus, or Sindbis virus, followed by gene transfer. A method using a retrovirus, adenovirus, adeno-associated virus, or vaccinia virus is particularly preferable. Examples of non-viral gene transfer methods include a method (DNA vaccine method) that involves direct intramuscular administration of an expression plasmid, a liposome method, a lipofectin method, a microinjection method, a calcium phosphate method, and an electroporation method. The DNA vaccine method and the liposome method are particularly preferable.

Examples of methods for causing the hair growth promoting agent, the hair regrowth promoting agent, and the therapeutic agent for alopecia for gene therapy to actually exert their effects as remedies include in vivo methods that involve direct introduction of DNA into bodies and ex vivo methods that involve removing cells of a certain type from humans, introducing DNA into the cells ex vivo, and then returning the cells into the bodies (Nikkei Science, April 1994, pp. 20-45; Gekkan Yakuji (The Pharmaceuticals Monthly), 36 (1), 23-48 (1994); and Extra Edition of Experimental Medicine, 12 (15) (1994)).

For example, when such gene-therapy agent is administered with the use of an in vivo method, the agent is administered via an appropriate route of administration depending on disease, symptoms, and the like, such as intravenous, intraarterial, subcutaneous, intradermal, and intramuscular administration. When such gene-therapy agent is administered with the use of an in vivo method, the gene-therapy agent is generally formulated as an injection or the like, or a commonly used carrier may be added to the agent, if necessary. Furthermore, when the agent is formulated in the form of a liposome or a membrane fusion liposome (e.g., a Sendai virus-liposome), the agent may be formulated into a liposome formulation such as a suspension, a freezing agent, or a centrifugal concentration freezing agent.

3. Application to in vitro Hair Regeneration System-1

An in vitro hair regeneration system for use in regenerated skin tissue can be established using full-length FGF-18 and/or partial peptides thereof. Here, "skin tissue" means tissue that is obtained by culturing isolated skin stem cells and is composed of various types of skin cells. Such "various types of skin cells" are not particularly limited and may include epidermal cells of the epidermis, cells of epidermal basal layers, various cells composing trichocysts, cells of dermis, fat cells, or the like. Cells to be used for skin tissue regeneration may be heterogeneic cells, allogeneic heterologous cells, or allogeneic autologous cells.

Methods for controlling the differentiation of skin stem cells into various types of skin cells are not particularly limited in the present invention, because of the absence of particularly standardized technology for this purpose. For example, growth factor receptors exhibiting different types of expression at a stage where natural differentiation (spontaneous differentiation) takes place may be used. Specifically, cells having different differentiation fates can be selectively amplified by adding ligand growth factors individually corresponding to such growth factors to a medium. After selective amplification of cells having different differentiation fates, skin tissues of interest can be prepared.

Methods for preparing artificial skin tissue are not particularly limited in the present invention, because of the absence of particularly standardized technology for this purpose. Examples from the variety of such methods that can be employed herein include a method that involves culturing epidermic cells alone so the cells assume into a laminar form, a method that involves forming a dermic layer with the use of cells composing dermis, such as fibroblasts, and then multi-layering epidermic cells for integration, a method that involves exposing the surface of such integrated epidermic cells to air, so as to promote epidermis formation, and a method that uses a laminar film formed of biodegradable components instead of using a dermic layer. Moreover, in the present invention, a method for preparing skin tissue, particularly in the field of so-called regenerative medicine is also applied, and involves isolating skin stem cells from skin tissue collected from a human and then preparing skin tissue using the isolated skin stem cells. At this time, new skin tissue may be prepared based on the premise that it is to be returned for treatment of the human from which such cells have been collected, or that it is to be transplanted for treatment of a human differing from the human from which such cells have been collected.

With the use of such method for preparing skin tissue, hair follicle growth can be promoted in skin tissue that has been regenerated with the addition of full-length FGF-18 and/or a partial peptide thereof into the relevant medium with appropriate timing. Furthermore, hair growth or hair regrowth can be promoted in skin tissue. Furthermore, with the use of such method for preparing skin tissue, skin cell growth can be promoted and the total skin volume can be increased with the addition of full-length FGF-18 and/or a partial peptide thereof into the relevant medium with appropriate timing.

4. Application to in vitro Hair Regeneration System-2

A culture method for hair follicle growth can be established using full-length FGF-18 and/or a partial peptide thereof. As hair follicles to be used herein, anagen human hair follicles prepared from pulled-out hair can be used, for example. Hair follicles are washed using an acceptable solution for washing, buffer, or medium. Examples of such acceptable solution for washing that can be used herein include, but are not particularly limited to, distilled water and a physiological saline solution. Examples of such acceptable buffer that can be used herein include, but are not particularly limited to, a phosphate buffer, phosphate buffered saline (PBS), phosphate buffered saline glucose, and Tris HCl. Examples of such acceptable medium that can be used herein include, but are not particularly limited to, Eagle's minimum essential medium, Eagle's basic medium, and Dulbecco's modified Eagle's medium. Dulbecco's modified Eagle's medium is preferable. Washed hair follicles are placed on cell culture plates at approximately 1 to approximately 10 hair follicles/well.

Hair follicles are generally cultured in a medium supplemented with heat-inactivated serum, preferably approximately 10% fetal calf serum, antibiotic (preferably 10,000 µl), penicillin G (approximately 10,000 µg), streptomycin sulfate, and approximately 1% Fungizone. Dulbecco's modified Eagle's medium is preferable as a selection medium. Hair follicles are cultured under approximately 5% $CO_2$ and approximately 95% atmospheric air at 37° C. for approximately 1 to approximately 5 days. At this time, full-length FGF-18 and/or a partial peptide thereof is added at approximately 0.01 to approximately 1.0 µg FGF/ml/day, for example. Moreover, heparin is added to each well at a ratio of heparin:FGF that is approximately 3:1. Human serum albumin (HSA) is added to all wells at a ratio of HSA:FGF that is approximately 10:1. Cell stimulation is performed by adding $^3$H-thymidine (approximately 5 µCi) at approximately 0.14 µg/well and then adding cold thymidine at approximately 14.2 µg/well during the final 24 hours of incubation. Thus, the effects of full-length FGF-18 and/or the partial peptide thereof can be examined.

Hair follicle DNA is precipitated with the use of approximately 5% trichloroacetic acid and then dissolved overnight in approximately 1N NaOH at approximately 45° C. Measurement using a scintillation counter is performed 3 times for each final cleavage product with a volume of 50 µl thereof. Full-length FGF-18 and/or a partial peptide thereof promotes DNA synthesis in hair follicles. Hence, ability to promote hair follicle growth can be revealed by assaying the amount of hair follicle DNA as described above.

5. Screening Method

The screening method according to the present invention is a method for screening for substances capable of exerting functions for hair growth promotion, hair regrowth promotion, treatment of alopecia, and the like via the effect of promoting hair follicle growth exerted by FGF-18.

In the screening method, first a test substance is caused to come into contact with cultured animal cells or experimental animals. In addition, the term "experimental animals" means non-human animals, such as mice, rats, chickens, turkeys, cattle, pigs, sheep, and rabbits. Examples of such test substances include, but are not particularly limited to, peptides, proteins, non-peptide compounds, low molecular weight compounds, synthetic compounds, fermentation products, cell extracts, and animal tissue extracts. These substances may be novel substances or known substances.

Next, in the screening method, FGF-18 gene expression is monitored in cultured animal cells or experimental animals. FGF-18 gene expression in cultured animal cells or experimental animals can be monitored by conducting analysis using a standard method such as ELISA using an FGF-18 antibody or conducting analysis on the mRNA levels of an FGF-18 gene within the cells or experimental animals through the use of a quantitative reverse transcription PCR method, a Northern blot method, or the like, for example.

When any of these analyses reveals that FGF-18 gene expression levels in cultured animal cells (cultured in the presence of a test substance or in experimental animals) are increased to levels greater than those of the same in cultured animal cells (cultured in the absence of the test substance), it can be concluded that the test substance possibly has functions of promoting hair growth, promoting hair regrowth, or treating alopecia.

When the substance thus screened for is clinically applied, the above active ingredient can be used alone or can also be used as a pharmaceutical composition through mixing with a pharmaceutically acceptable carrier. The proportion of an active ingredient to a carrier at this time can be varied as being from 1% to 90% by weight. Furthermore, such drug can be administered in various forms. Examples of such forms for administration include solutions, creams, ointments, gel, lotions, shampoos, and aerosol preparations for parenteral administration. In addition, the dose can be appropriately selected depending on symptoms, age, body weight, and the like.

EXAMPLES

The present invention will be further described specifically with reference to examples. However, the technical scope of the present invention is not limited by the following examples.

Example 1

In this Example, the expression profiles of genes belonging to the FGF family in the mouse skin were examined.

<Materials and Methods>

Mice and Skin Sample Preparation

For hair cycle experiments, twenty-five 7-week-old male C3H/HeN mice (Tlr4$^{+/+}$) were obtained from Japan SLC and maintained on a standard laboratory diet and water ad libitum. After conditioning for 1 week, 5 mice were sacrificed, the dorsal hair thereof was cut short, and skin samples were isolated and examined as the "day 0 (telogen)" samples. In the remaining 20 mice, anagen of the hair growth cycle was induced by gently depilating the dorsal hair shafts with gloved fingers, but without using wax, tape, or depilatory chemicals. Then, at selected stages of the hair follicle cycle that is; on days 8 (anagen V), 18 (anagen VI), 20 (catagen IV), and 22 (telogen) after depilation), the mice were sacrificed and their hair was cut short. Full-thickness skin samples (including epidermis, hair shafts, hair follicles, sebaceous glands, subcutaneous adipose tissue, dermal muscles, and blood vessels) were collected from the depilated area. The thus obtained full-thickness skin samples were then used for mRNA isolation, in situ hybridization, or immunohistochemical staining described later. The experiment was carried out three times using essentially the same experimental design to confirm the reproducibility of the results.

For in situ hybridization, the skin samples were immediately embedded in optimum cutting temperature compounds (OCT-compounds) and then frozen using liquid nitrogen. For immunohistochemical staining, the skin samples were first fixed for 24 hours at room temperature in 10% formaldehyde and then paraffin-embedded via standard procedures.

mRNA Preparation and Reverse Transcription

Total RNA was prepared from the above-prepared skin samples using Isogen (Nippon Gene) according to the manufacturer's instructions. Next, the mRNA was purified from the total RNA using an Oligotex-dT30 Super mRNA purification kit (Takara Bio). A reverse transcription reaction (at a total volume of 20 ml) was carried out using each of the thus purified mRNA samples (100 ng) as a template and SuperScript II with Oligo (dT)$_{12-18}$ as a primer (Gibco BRL).

Design of PCR Primers and the Cloning of FGF cDNA

Specific primer sets were designed (Table 1) so that each FGF mRNA level could be analyzed using real-time PCR. cDNA fragments are required as copy number references when such FGF mRNA levels are quantified. The same primer sets were also used for cloning the respective cDNA fragments that served as copy number references for quantification.

TABLE 1

| | Sequence(5'-3') | SEQ ID NO: |
|---|---|---|
| FGF-1 | CTGACCGAGAGGTTCAACCTGCCTCTAGGA | SEQ ID NO:6 |
| | CTTTATATACACTTCGCCCGCACTTTCCGC | SEQ ID NO:7 |
| FGF-2 | GCGACCCACACGTCAAACTACAACTCCAAG | SEQ ID NO:8 |
| | CCCGTTTTGGATCCGAGTTTATACTGCCCA | SEQ ID NO:9 |
| FGF-3 | ACGGCTGTATGCTTCGGATCACTACAACGC | SEQ ID NO:10 |
| | GCCATTCACCGACACGTACCAAGGTCTCTG | SEQ ID NO:11 |
| FGF-4 | GACACGAGGGACAGTCTTCTGGAGCTCTCT | SEQ ID NO:12 |
| | CCGTTCTTACTGAGGGCCATGAACATACCG | SEQ ID NO:13 |
| FGF-5 | ACCTATGCGTCCGCGATCCACAGAACTGAA | SEQ ID NO:14 |
| | AAGTTCCGGTTGCTCGGACTGCTTGAACCT | SEQ ID NO:15 |
| FGF-6 | GCACTGAGCAAATATGGACGGGTAAAGCGG | SEQ ID NO:16 |
| | AGTCACGGGATAGGAGCAGAAGCGTTCTCT | SEQ ID NO:17 |

TABLE 1-continued

| | Sequence(5'-3') | SEQ ID NO: |
|---|---|---|
| FGF-7 | TGGAAATCAGGACCGTGGCAGTTGGAATTG | SEQ ID NO:18 |
| | GATTTAAGGCAACGAACATTTCCCCTCCGC | SEQ ID NO:19 |
| FGF-8 | ATACTTTTGGAAGCAGAGTCCGAGTTCGCG | SEQ ID NO:20 |
| | GGTAAAGGCCATGTACCAGCCCTCGTACTT | SEQ ID NO:21 |
| FGF-9 | TAGGTGAAGTTGGGAGCTATTTCGGTGTGC | SEQ ID NO:22 |
| | CCCTTTAAATGATCCAAGTCCGTGACTGCG | SEQ ID NO:23 |
| FGF-10 | AAGCTCTTGGTCAGGACATGGTGTCACAGG | SEQ ID NO:24 |
| | GTACGGACAGTCTTCATTCTTGGTCCCGCT | SEQ ID NO:25 |
| FGF-11 | AGCTCAAAGGCATCGTCACCAAACTGTTCT | SEQ ID NO:26 |
| | GCTGTGAAATGTGGCGAGCTGTACAATAGC | SEQ ID NO:27 |
| FGF-12 | TGTGACAAGGTTATTCAGCCAGCAGGGATA | SEQ ID NO:28 |
| | ATAAAGGCTGGCTTTAACCCCTTGGATGGC | SEQ ID NO:29 |
| FGF-13 | GGCAATGAACAGCGAGGGATACTTGTACAC | SEQ ID NO:30 |
| | CGGATTGCTGCTGACGGTAGATCATTGATG | SEQ ID NO:31 |
| FGF-14 | CGGGCTTTTCAATGGCAACCTGGTGGATAT | SEQ ID NO:32 |
| | TACAACCCTGTCTTCACTCCCTGGATGGCA | SEQ ID NO:33 |
| FGF-15 | TGGATCCGTTCAGGATGGTGGAGGATGTAG | SEQ ID NO:34 |
| | AGCCACTAACACAACAGGGTCCATGTGAGA | SEQ ID NO:35 |
| FGF-16 | CCCGGGAGGGATACAGGACTAAACGACACC | SEQ ID NO:36 |
| | AGCGGAAGAGATCTCTGGACATGGAGGGCA | SEQ ID NO:37 |
| FGF-17 | CAGTACGTGAGGGACCAGGGCGCTATGACC | SEQ ID NO:38 |
| | CTCCACGATGAGCTTGGCGAACTTGTTGCC | SEQ ID NO:39 |
| FGF-18 | AGACGCGGGCTCGAGATGATGTGAGTCGGA | SEQ ID NO:40 |
| | GCCCTTGATCCGGACTTGACTCCCGAAGGT | SEQ ID NO:41 |
| FGF-20 | AGTGTGGCAGTGGGACTGGTCAGTATCAGA | SEQ ID NO:42 |
| | TAAGTGCTACAAAATACCTGCGACCCGTGT | SEQ ID NO:43 |
| FGF-21 | GAGATCAGGGAGGATGGAACAGTGGTAGGC | SEQ ID NO:44 |
| | GGGCTTCAGACTGGTACACATTGTAACCGT | SEQ ID NO:45 |
| FGF-22 | CGTAGGGGTGTTCTGGGTCTTCTCCATGAA | SEQ ID NO:46 |
| | TTCATGGAGAAGACCCAGAACACCCCTACG | SEQ ID NO:47 |
| FGF-23 | AGCCAGGACCAGCTATCACCTACAGATCCA | SEQ ID NO:48 |
| | GCAATTCTCTGGGCTGAAGTGAAGCGATCC | SEQ ID NO:49 |

The RT mixture (the reaction product of the above reverse transcription reaction) was diluted ten-fold (1:10) with distilled water. The resultant was used as a template for PCR amplification. PCR amplification was carried out using Pfu polymerase (Stratagene) according to the manufacturer's instructions. Thereafter, aliquots of the PCR amplification reaction mixture were applied to 2.0% agarose gel electrophoresis to confirm the sizes of the amplified products. To clone the cDNA corresponding to each FGF, the PCR products were ligated to pCR-Blunt II-TOPO vectors (Invitrogen). The vectors were then used to transform *Escherichia coli*. The nucleotide sequences of the recombinant plasmids were verified using a BigDye terminator cycle sequencing kit and an ABI PRISM 310 Genetic Analyzer (Applied Biosystems).

Quantification of mRNA Copy Number by Real-time PCR

Real-time PCR amplification was carried out in a Light Cycler (Roche Diagnostics) using 2 ml of an RT mixture diluted ten-fold (1:10) as a template. The absolute copy number of each FGF was determined using a plasmid DNA corresponding to each FGF as a copy number reference. Cyber Green was used for quantification of the amplified DNA using a Light Cycler. Light Cycler reactions were carried out using highly specific primers, as well as optimized annealing temperatures, elongation time, and acquisition temperatures. Initially, the specificity of the primers was confirmed using the whole mouse cDNA sequence as the background sequence. Primer specificity and reaction conditions were further experimentally confirmed through cloning of an amplified fragment into a plasmid DNA, so that the sequences thereof were verified.

At the end of the individual experiments, the melting temperatures of the amplified products were measured to confirm their homogeneity. After the quantification experiments, the products were analyzed by 2.0% agarose gel electrophoresis to confirm that DNA fragments of known sizes had been amplified as expected by the reactions. Specific quantification of individual genes is guaranteed with the use of such experimental system. For the evaluation of mRNA, a serially diluted DNA sample with the target cDNA sequence was included in the same experiment using a Light Cycler. From these measurements, the absolute copy number of the mRNA of interest associated with each sample was calculated. The copy number of the housekeeping gene was also evaluated using the same procedures. Thus, it was confirmed that such amounts of copies were within the expected range (for example, the b-actin mRNA copy number was measured to be $2 \times 10^6$ copies/ng mRNA in the case of the sample on day 8).

<Results>

Expression Profiles of FGF and FGFR Family Members

Figure 1B:
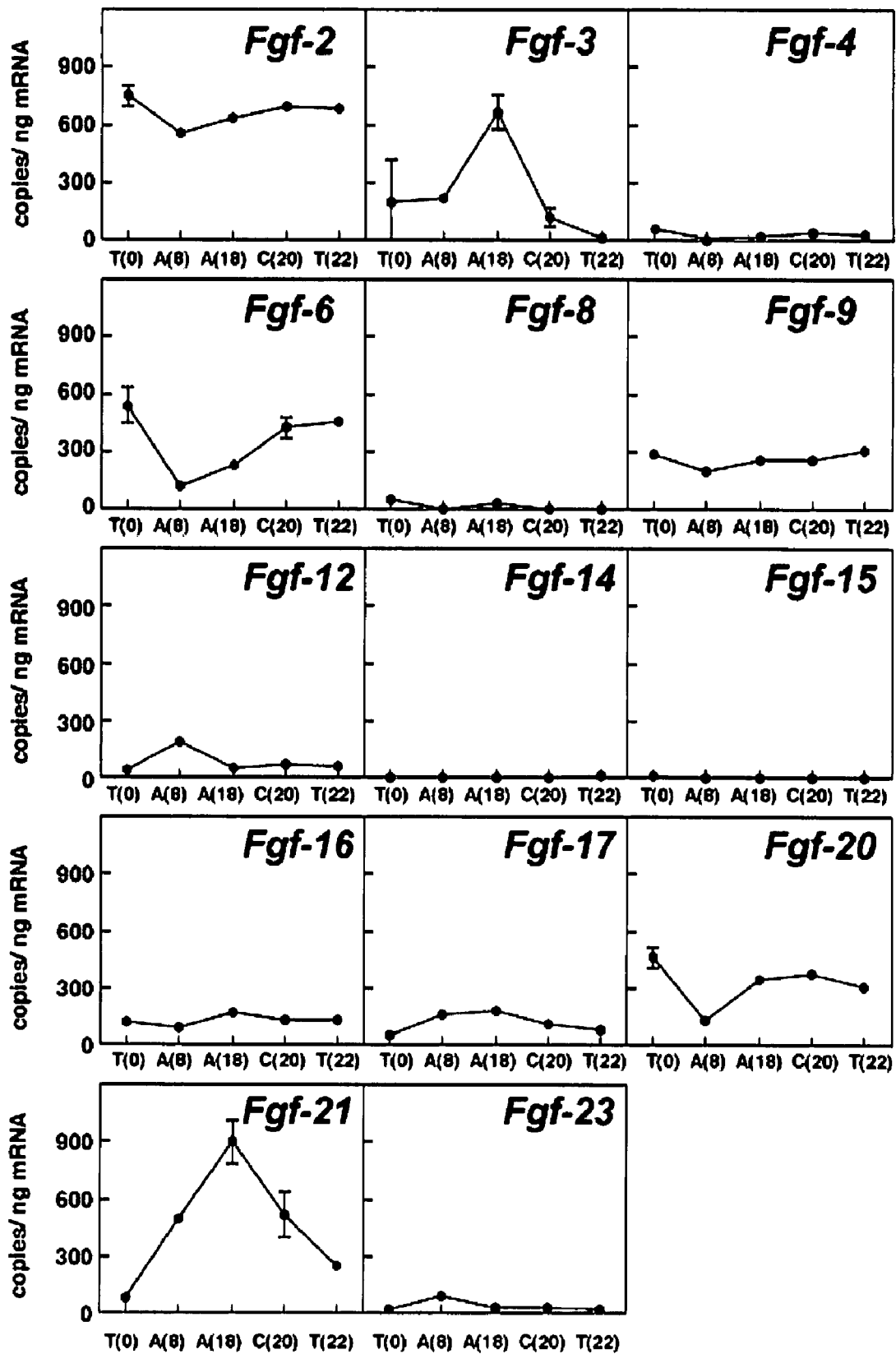
FIG. 1B shows characteristic graphs showing the expression profiles of FGF-2, -3, -4, -6, -8, -9, -12, -14, -15, -16, -17, -20, -21, and -23 genes during each hair cycle.
Figure 2:
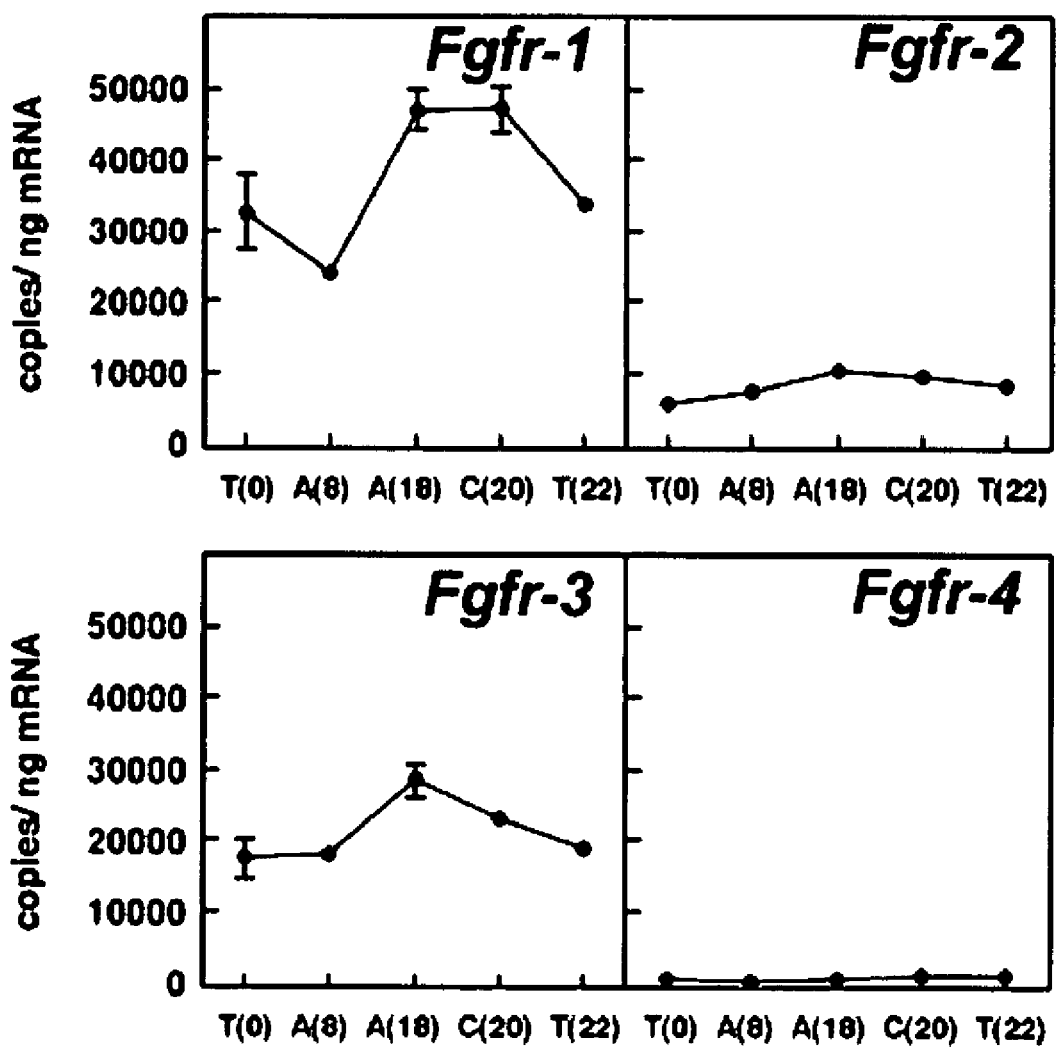
FIG. 2 shows characteristic graphs showing the expression profiles of genes belonging to the FGFR family during each hair cycle.

The expression levels of FGF and FGFR mRNA at the indicated stages in the hair cycle are shown in FIG. 1A, FIG. 1B, and FIG. 2, respectively. In addition, the highest expression levels of all the mRNAs and the stages of the hair cycle during which such expression levels were observed are summarized in Table 2.

TABLE 2

| | Highest mRNA expression level | |
|---|---|---|
| Gene | Copy number (Copies/ng mRNA) | Phase of the hair cycle at which the highest mRNA expression level was attained (Days after depilation) |
| Fgf-1 | 2,900 +/− 136 | Telogen (0) |
| Fgf-2 | 751 +/− 46 | Telogen (0) |
| Fgf-3 | 667 +/− 77 | Anagen VI (18) |
| Fgf-4 | (—) | (—) |
| Fgf-5 | 1,882 +/− 273 | Anagen VI (18) |
| Fgf-6 | 542 +/− 84 | Telogen (0) |
| Fgf-7 | 7,467 +/− 424 | Anagen V (8) |
| Fgf-8 | (—) | (—) |
| Fgf-9 | 306 +/− 30 | Telogen (22) |
| Fgf-10 | 4,389 +/− 305 | Anagen V (8) |
| Fgf-11 | 1,422 +/− 75 | Telogen (0) |
| Fgf-12 | 188 +/− 21 | Anagen V (8) |
| Fgf-13 | 4,945 +/− 77 | Telogen (0) |
| Fgf-14 | (—) | (—) |
| Fgf-15 | (—) | (—) |
| Fgf-16 | 171 +/− 30 | Anagen VI (18) |
| Fgf-17 | 179 +/− 6 | Anagen VI (18) |
| Fgf-18 | 9,822 +/− 1,677 | Telogen (0) |
| Fgf-20 | 465 +/− 45 | Telogen (0) |
| Fgf-21 | 898 +/− 98 | Anagen VI (18) |
| Fgf-22 | 2,685 +/− 275 | Anagen VI (18) |
| Fgf-23 | (—) | (—) |
| Fgfr-1 | 47,108 +/− 2,758 | Catagen (20) |
| Fgfr-2 | 10,414 +/− 1,055 | Anagen VI (18) |
| Fgfr-3 | 28,540 +/− 2,015 | Anagen VI (18) |
| Fgfr-4 | 1,028 +/− 191 | Catagen (20) |
| Beta-actin | 562,240 +/− 36,592 | Anagen V (8) |

The genes expressed at the highest levels were Fgf-1, -5, -7, -10, -13, -18, and -22, as shown in FIG. 1A and Table 2. Within this group, the levels of FGF-5 and FGF-22 mRNA exhibited similar variation throughout the hair cycle, with the highest expression levels during anagen VI (day 18: FIG. 1A). The levels of FGF-7 and FGF-10 mRNA (or keratinocyte growth factor (KGF) 1 and KGF-2, respectively) were found to be the highest during anagen V (day 8; FIG. 1A). The level of FGF-1 mRNA (or acidic FGF) was comparatively constant, with maximum levels during telogen (day 0; FIG. 1A). The highest expression level of FGF (e.g., FGF-7 or -18) was approximately $1 \times 10^4$ copies/ng mRNA. This mRNA expression level was about 60 times lower than that of β-actin ($5.6 \times 10^5$ copies/ng mRNA during anagen V; Table 2), one of the abundant structural proteins in skin.

In this Example, it was revealed that, in addition to these genes (FGF-1, -2, -5, -7, -10, -13, and -22) already known to be expressed in skin, FGF-18 mRNA was also expressed at high levels and the FGF-18 mRNA levels peaked during telogen (days 0 and 22; FIG. 1A). Furthermore, during most stages, the FGF-18 expression levels were higher than those of well-studied FGF-2 (or basic FGF) and those of other FGFs, as is clear from FIG. 1A. FGF-3, -6, -9, -11, -20, and -21 mRNA were also expressed at moderate levels (FIG. 1B), but little or no expression of FGF-4, -8, -14, -15, and -23 mRNA was detected at any stage of the hair cycle (<100 copies/ng mRNA; Table 2).

With respect to FGFR, both FGFR-1 mRNA and FGFR-3 mRNA were abundantly expressed (a maximum of 47,000 copies/ng mRNA for FGFR-1 or 28,000 copies/ng mRNA for FGFR-3; FIG. 2). The strongest expression of the former occurred during anagen VI-catagen (days 18 and 20), whereas that of the latter peaked during anagen VI (day 18; FIG. 2). The expression levels of FGFR-2 mRNA, including its IIIb subclass that is specific to epithelial cells, were lower than those of either FGFR-1 or -3 mRNA (FIG. 2). The expression levels of FGFR-4 mRNA were the lowest among those of 4 types of receptors (FIG. 2).

Example 2

In Example 1, FGF-18 expression in skin was revealed. The mRNA distribution was measured using in situ hybridization in this Example.

<Materials and Methods>

In situ Hybridization

The in situ hybridization experiments were carried out using OCT-embedded frozen tissue sections and digoxygenin-labeled riboprobes essentially as reported previously (see Komminoth P: Digoxygenin as an alternative probe labeling for in situ hybriodization, Diag. Mol. Pathol. 1: 142-150, 1992).

Sense and antisense riboprobes for FGF18 were synthesized using SP6 and T7 RNA polymerases, respectively, in the presence of digoxygenin-dUTP (Roche Applied Science). All possible efforts were made to avoid RNA degradation during the hybridization procedure. The frozen tissues were cut into 10-mm sections using a Cryostat (Microm, model HM5000M), immediately placed on MAS-coated slide glasses (Matsunami Glass), dried at 50° C. for 1 hour, and then stored at −80° C. with a desiccant. Before hybridization, the sections were fixed in 4% paraformaldehyde in PBS for 10 minutes at room temperature and then washed with PBS for 5 minutes. Thereafter, the sections were permeabilized with proteinase K (0.01 mg/ml in 2×TE) for 5 minutes at 37° C., rinsed with PBS, again fixed with 4% paraformaldehyde in PBS for 5 minutes, and washed with PBS for 5 minutes. The fixed sections were soaked twice in 0.1% DEPC in PBS for 15 minutes and then rinsed with PBS.

The sections were then soaked in 100% formamide at 45° C. for 10 minutes, rinsed with 100% formamide and 50% formamide at 45° C., and then soaked in 5×SSC for 15 minutes. Finally, hybridization was carried out for 16 to 18 hours at 45° C. using a heat-denatured (70° C. for 10 minutes) probe added at 500 ng/ml to 100 ml of a hybridization buffer containing 50% (v/v) formamide, 5×SSC, 500 mg/ml salmon testes DNA, 250 mg/ml tRNA, 5×Denhardt's solution, and 1 mM DTT. After hybridization, the slides were rinsed with 2×SSC at 45° C. and then washed twice with 2×SSC for 30 minutes at 45° C. and twice with 0.2×SSC for 20 minutes at 45° C. The bound riboprobe was detected using an anti-digoxygenin antibody conjugated with alkaline-phosphatase (1:500, Roche Applied Science). For visualization, a colorimetric reaction with nitro-blue tetrazolium and 5-bromo-4-chloro-3-indolyl-1-phosphate (NBT/BCIP) was carried out using BM Purple (Roche Applied Science) at room temperature in the dark until purple signals developed. Specifically, section samples obtained on day 8 (anagen V) after depilation were subjected to 24 hours of a colorimetric reaction. Section samples obtained on day 18 (anagen VI) after depilation were subjected to 48 hours of a colorimetric reaction. Section samples obtained on day 20 (catagen IV) were subjected to 24 hours of a colorimetric reaction. Section samples obtained on day 0 (telogen) were subjected to 96 hours of a colorimetric reaction.

<Results>

Figure 3:
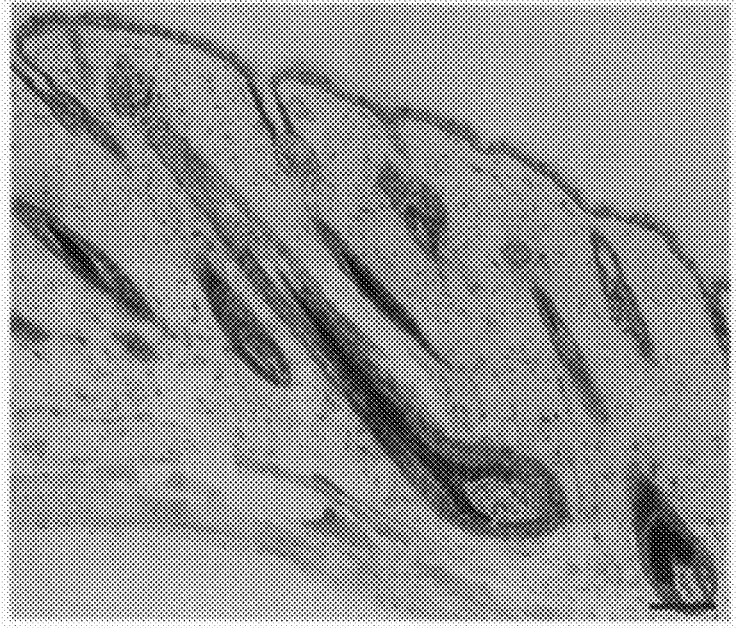
FIGS. 3A-3D represent photographs showing the results of in situ hybridization experiments.
Figure 3:
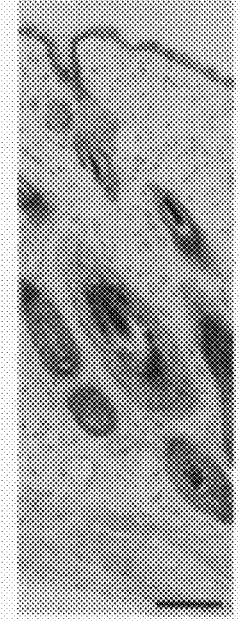
Figure 3:
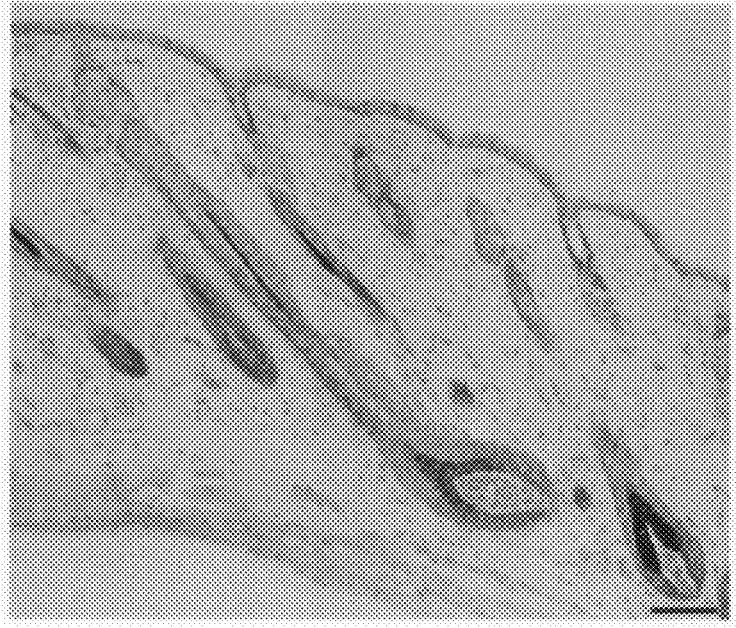
Figure 3:
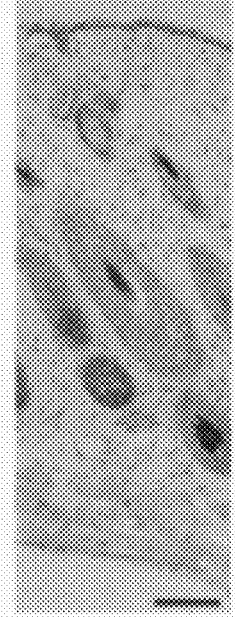

FIGS. 3A-3D shows the results of in situ hybridization. FIGS. 3A-3B show the results obtained using antisense riboprobes. FIGS. 3C-3D show the results obtained using sense probes. Each bar in FIGS. 3A-3D denotes 100 μm. As shown in FIGS. 3A-3B, FGF-18 mRNA was expressed virtually exclusively in the inner root sheath cells of the hair follicles in their growth stage (purple signals). In contrast, as shown in FIGS. 3C-3D the sense probes produced no signals.

During telogen, FGF-18 mRNA expression was observed in the bulge region at the hair follicle bottom. In addition, during telogen, even β-actin mRNA is detected very weakly at best. Hence, it was very difficult to carry out in situ hybridization during telogen compared with that carried out during anagen. Therefore, in this Example, it was made possible to carry out in situ hybridization during telogen by subjecting section samples on day 0 (telogen) to a lengthy colorimetric reaction (as long as 96 hours) for in situ hybridization.

Example 3

In this Example, to evaluate the functions of FGF-18 in skin, the effect of FGF-18 to promote cell division was examined for outer root sheath (ORS) cells of human follicles, human hair papilla (HFDP: human hair follicle dermal papilla) cells, human dermal fibroblasts (HDF cells), and human epidermal keratinocytes (HEK cells).

<Materials and Methods>

DNA Synthesis Assays

Cultured primary human dermal fibroblasts (derived from newborn foreskin; Toyobo) were subcultured in HDF growth media (fibroblast basal medium (FBM) with growth supplements; Toyobo). The resultant cells were used within two passages for [$^3$H]-thymidine incorporation assays.

Cultured primary human hair papilla cells (derived from adult scalp, Toyobo) were subcultured in HFDP growth media (hair papilla cell basal medium containing 20% fetal calf serum; Toyobo). The resultant cells were used within two passages for [$^3$H]-thymidine incorporation assays. The cells were trypsinized and dispensed into a 48-well (HDF cells) collagen-coated plate (Sumilon) at a density of 1×10$^4$ cells/well or into a 24-well (HFDP cells) collagen-coated plate at a density of 1×10$^4$ cells/well. Then the resultants were maintained in HDF media at 37° C. On the next day, the HDF growth media were replaced with FBM containing 0.5% charcoal-absorbed calf serum. The cells were cultured for 48 hours (HDF cells) or 96 hours (HFDP cells), followed by stimulation with FGF of a predetermined concentration. 18 hours (HDF cells) or 8 hours (HFDP cells) after addition of FGF, [$^3$H]-thymidine (1 mCi/well; Moravek Biochemicals) was added to the media. The cells were further cultured for 8 hours (HDF cells) or 18 hours (HFDP cells). The cells were then harvested, and the incorporated radioactivity was counted.

Cultured primary human epidermal keratinocytes (derived from newborn foreskin; Toyobo) and primary human outer root sheath cells (derived from adult male scalp) were subcultured in keratinocyte growth media (keratinocyte basal medium (KBM)-2 supplemented with a bovine pituitary extract, insulin, an epidermal growth factor, hydrocortisone, transferrin, epinephrine, and antibiotics; Toyobo) and then used within two passages. The cells were trypsinized and then dispensed into a 48-well (HEK cells) collagen-coated plate at a density of 1×10$^4$ cells/well or a 24-well (ORS cells) collagen-coated plate at a density of 1.2×10$^4$ cells/well. The cells were then maintained in HEK growth media at 37° C. On the next day (HEK cells) or 4 days later (ORS cells), each growth medium was replaced with a KBM-2 medium containing 10$^{-8}$ M insulin and 5 mg/ml heparin, followed by stimulation with FGF of a predetermined concentration. 18 hours (HEK cells) or 8 hours (ORS cells) after addition of FGF, [$^3$H]-thymidine (1 mCi/0.5 ml; Moravek Biochemicals) was added to the medium. The cells were further cultured for 8 hours (HEK cells) or 18 hours (ORS cells). The cells were then harvested, and the incorporated radioactivity was counted.

<Results>

Figure 4:
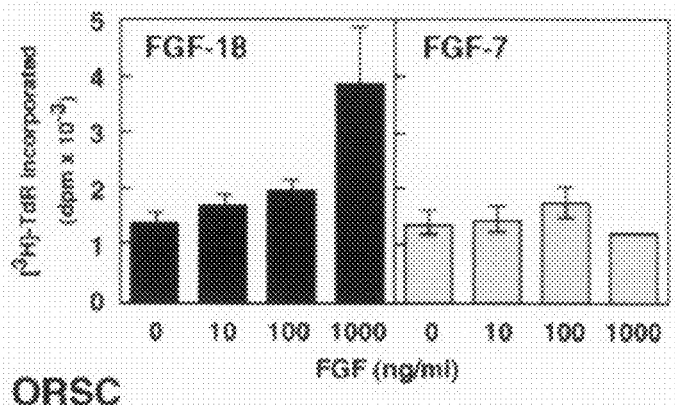
FIGS. 4A-4D represent characteristic graphs showing the results of DNA synthesis assays.
Figure 4:
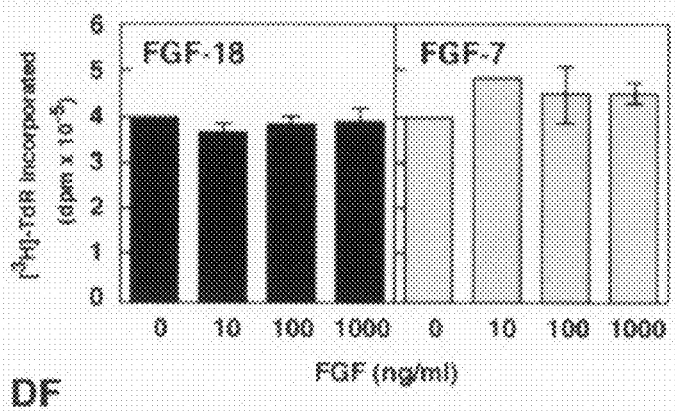
Figure 4:
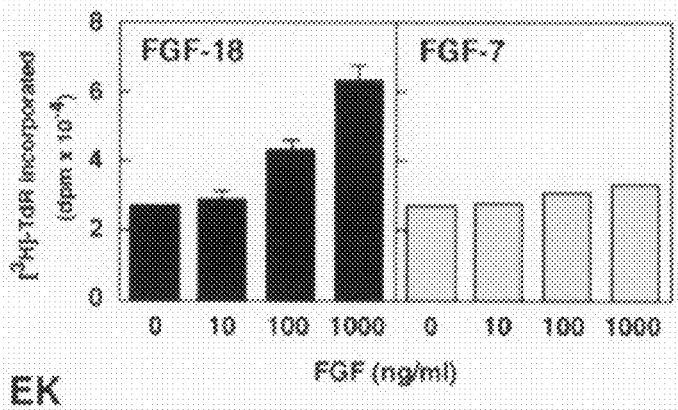
Figure 4:
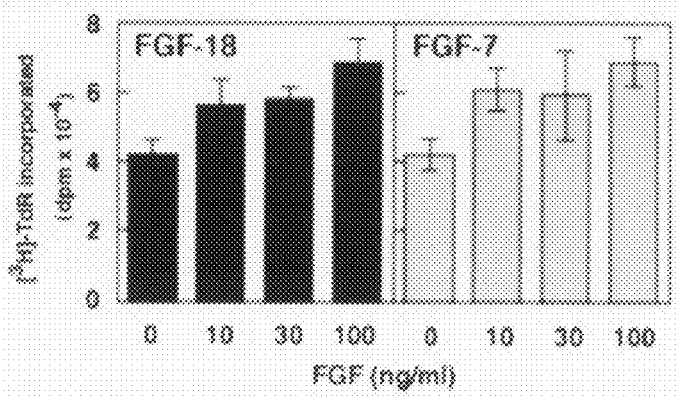

FIGS. 4A-4D shows the results of DNA synthesis assays. FIG. 4A shows the results of assays using HFDP cells (denoted as DPC). FIG. 4B shows the results of assays using ORS cells (denoted as ORSC). FIG. 4C shows the results of assays using HDF cells (denoted as DF). FIG. 4D shows the results of assays using HEK cells (denoted as EK). At relatively high concentrations FGF-18 (100 ng/ml and 1000 ng/ml) induced DNA synthesis in HFDP cells, HDF cells, and HEK cells (shown in FIGS. 4A, 4C, and 4D respectively). These results differ from the results in the case of FGF-7 (KGF), the keratinocyte mitogen.

Specifically, keratinocyte mitogens were sufficiently characterized by their stimulation of DNA synthesis in HEK cells (FIG. 4D), but they displayed extremely weak stimulation of DNA synthesis in HFDP cells (FIG. 4A) and HDF cells (FIG. 4C).

These results demonstrated that the full-length FGF-18 and/or partial peptides thereof have the effect of promoting hair follicle growth. Furthermore, these results also demonstrated that the full-length FGF-18 and/or partial peptides thereof exert the effect of promoting skin cell growth; that is, promoting increases in total skin volume.

Example 4

In this Example, to examine the characteristics of the effects of FGF-18 on hair follicles in vivo, the effects resulting from administration of FGF-18 were tested in C3H/HeN mice during telogen stage of the hair cycle.

<Materials and Methods>

In vivo Analysis of FGF-18 Activity

To examine the characteristics of the effects of FGF-18 on hair follicles in vivo, recombinant FGF-18 was administered to mice that were undergoing telogen stage of hair growth. The in vivo activity of macrophage-stimulating protein was demonstrated according to the basic protocol developed by McElwee et al (see McElwee K J, Huth A, Kissling S, Hoffman R; Macrophage-stimulating protein promotes hair growth ex vivo and induces anagen from telogen stage hair follicles in vivo, J. Invest. Dermatol. 123: 34-40, 2004).

Specifically, 0.75 ml of PBS supplemented with 10 mg of a recombinant FGF-18 protein was mixed with 0.75 ml (packed volume) of Sepharose 4B beads and 7.5 ml of C3H/HeN serum and incubated at 37° C. for 2 hours. Thus, the recombinant FGF-18 was adsorbed to the beads. Control beads were obtained by carrying out the same procedure without adding any recombinant FGF-18. Five 50-day-old female C3H/HeN mice were then anesthetized and their dorsal hair was gently cut short with a trimmer. The FGF-18-adsorbed bead suspension was injected subcutaneously into the dorsal region (150 ml/mouse; i.e., 1 µg of FGF-18 per mouse). The mice were then maintained on a standard laboratory diet and water ad libitum. 21 days later, the mice were then anesthetized and then sacrificed. The full thickness of the dorsal skin was excised and then its reverse side was photographed. Each skin sample was paraffin-embedded. The embedded skin samples were cut into 4 µm-thick sections using a microtome, stained with hematoxylin, and then observed under a microscope.

<Results>

Figure 5:
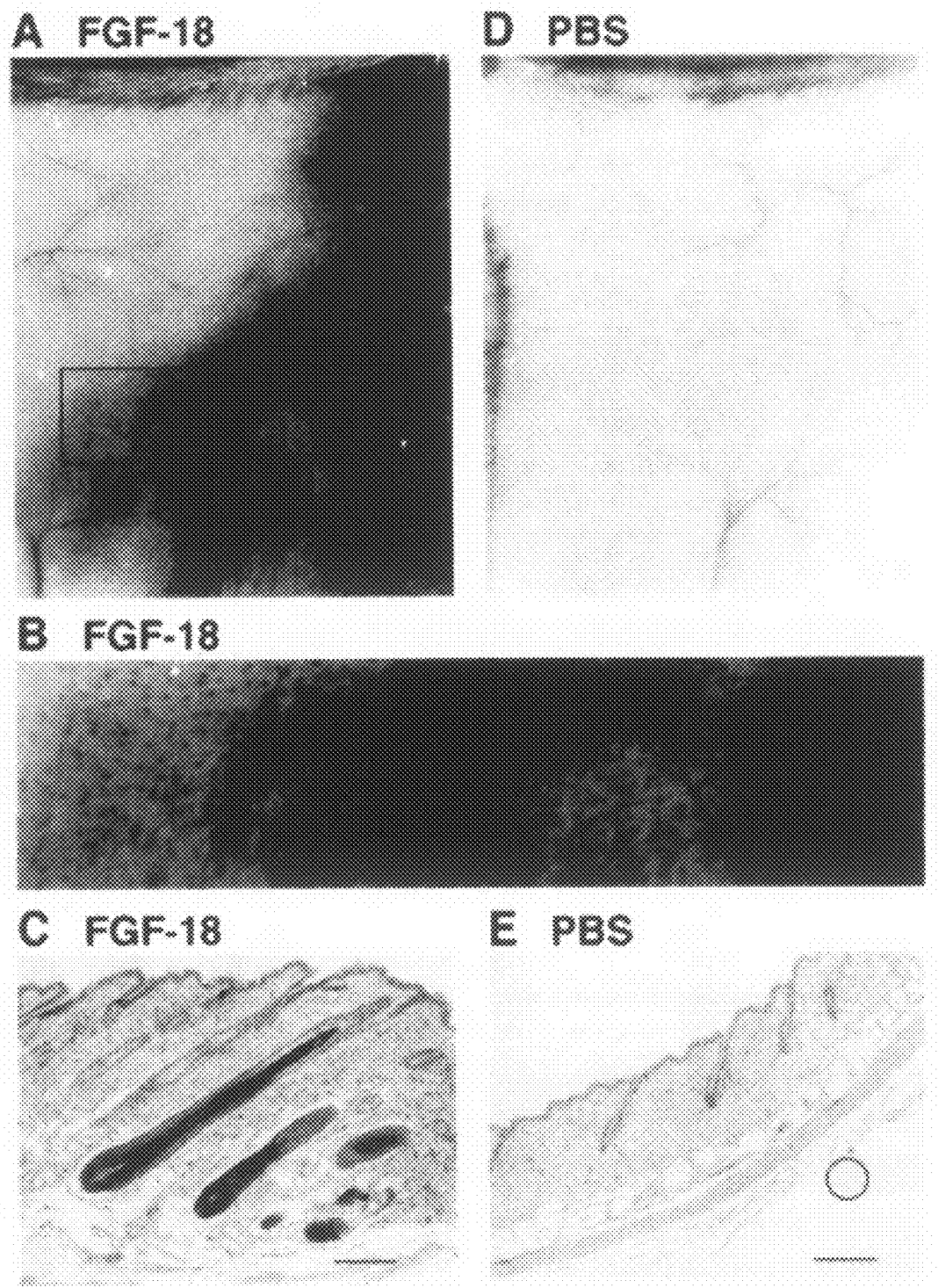
FIGS. 5A-5E represent photographs showing the results of in vivo analytical tests conducted on FGF-18 activity.

FIGS. 5A-5E shows the results. FIG. 5A is a photograph showing the reverse side of the resected skin of a mouse that had received the FGF-18-adsorbed bead suspension. FIG. 5B is an enlarged photograph showing the square area within FIG. 5A. FIG. 5C is a photograph showing the skin section of a mouse that had received the FGF-18-adsorbed bead suspension. FIG. 5D is a photograph showing the reverse side of the resected skin of a mouse that had received the control bead suspension. FIG. 5E is a photograph showing the skin section of a mouse that had received the control bead suspension. In addition, bars in FIGS. 5C and 5E each denote 100 µm.

21 days after subcutaneous administration of the FGF-18-adsorbed bead suspension, 4 out of 5 mice exhibited hair follicle growth. The exterior surface of the dorsal skin of one mouse exhibited vigorous hair growth throughout the test area, whereas the other 3 mice exhibited clear pigmentation in various parts of the test area (photographs not shown).

Examination of the reverse side of the skin revealed extensive growth of anagen hair follicles in the mice with clear pigmentation and/or hair growth (FIGS. 5A-5B). Photographs A and B in FIGS. 5A-5B show typical results (dark spots indicate anagen hair follicles). Furthermore, as shown in photograph C in FIG. 5C, extensive growth of mouse anagen hair follicles could also be confirmed by histological examination conducted for the skin sections. Furthermore, 1 out of 5 mice that had received the FGF-18-adsorbed bead suspension showed no apparent changes during the test period.

In contrast, none of the skin samples obtained from 5 control mice that had received the control bead suspension exhibited hair growth or strong pigmentation.

As shown in photograph D in FIG. 5D, examination of the reverse sides of the control skin samples revealed the absence of or presence of only a few anagen hair follicles, as is indicated by the white color. It was possible to confirm this by histological examination, as shown in photograph E in FIG. 5E.

Based on these results, it was demonstrated in vivo that hair follicle growth can be promoted through administration of full-length FGF-18 and/or partial peptides thereof.

Furthermore, as is clear from comparison between FIGS. 5C, and 5E, the skin became very thick, as in the case of normal skin having physiological anagen hair follicles. Based on the results, it was demonstrated that full-length FGF-18 and/or partial peptides thereof exert the effect of promoting skin cell growth; that is, promoting increases in total skin volume.

Sequence Listing

The invention claimed is:

1. A composition comprising a full-length FGF-18 or a biologically active partial peptide thereof, and at least one member selected from the group consisting of an anti-androgen, a 5α-reductase inhibitor and minoxidil.

2. The composition according to claim 1, further comprising another protein growth factor and/or a hair growth promoting agent.

* * * * *

SEQUENCE LISTING

```
<160> NUMBER OF SEQ ID NOS: 49

<210> SEQ ID NO 1
<211> LENGTH: 624
<212> TYPE: DNA
<213> ORGANISM: Homo sapiens
<220> FEATURE:
<221> NAME/KEY: CDS
<222> LOCATION: (1)..(624)

<400> SEQUENCE: 1 atg tat tca gcg ccc tcc gcc tgc act tgc ctg tgt tta cac ttc ctg      48
Met Tyr Ser Ala Pro Ser Ala Cys Thr Cys Leu Cys Leu His Phe Leu
1               5                   10                  15 ctg ctg tgc ttc cag gta cag gtg ctg gtt gcc gag gag aac gtg gac      96
Leu Leu Cys Phe Gln Val Gln Val Leu Val Ala Glu Glu Asn Val Asp
            20                  25                  30 ttc cgc atc cac gtg gag aac cag acg cgg gct cgg gac gat gtg agc     144
Phe Arg Ile His Val Glu Asn Gln Thr Arg Ala Arg Asp Asp Val Ser
        35                  40                  45
```

```
cgt aag cag ctg cgg ctg tac cag ctc tac agc cgg acc agt ggg aaa      192
Arg Lys Gln Leu Arg Leu Tyr Gln Leu Tyr Ser Arg Thr Ser Gly Lys
 50                  55                  60 cac atc cag gtc ctg ggc cgc agg atc agt gcc cgc ggc gag gat ggg      240
His Ile Gln Val Leu Gly Arg Arg Ile Ser Ala Arg Gly Glu Asp Gly
 65                  70                  75                  80 gac aag tat gcc cag ctc cta gtg gag aca gac acc ttc ggt agt caa      288
Asp Lys Tyr Ala Gln Leu Leu Val Glu Thr Asp Thr Phe Gly Ser Gln
                 85                  90                  95 gtc cgg atc aag ggc aag gag acg gaa ttc tac ctg tgc atg aac cgc      336
Val Arg Ile Lys Gly Lys Glu Thr Glu Phe Tyr Leu Cys Met Asn Arg
            100                 105                 110 aaa ggc aag ctc gtg ggg aag ccc gat ggc acc agc aag gag tgt gtg      384
Lys Gly Lys Leu Val Gly Lys Pro Asp Gly Thr Ser Lys Glu Cys Val
        115                 120                 125 ttc atc gag aag gtt ctg gag aac aac tac acg gcc ctg atg tcg gct      432
Phe Ile Glu Lys Val Leu Glu Asn Asn Tyr Thr Ala Leu Met Ser Ala
    130                 135                 140 aag tac tcc ggc tgg tac gtg ggc ttc acc aag aag ggg cgg ccg cgg      480
Lys Tyr Ser Gly Trp Tyr Val Gly Phe Thr Lys Lys Gly Arg Pro Arg
145                 150                 155                 160 aag ggc ccc aag acc cgg gag aac cag cag gac gtg cat ttc atg aag      528
Lys Gly Pro Lys Thr Arg Glu Asn Gln Gln Asp Val His Phe Met Lys
                165                 170                 175 cgc tac ccc aag ggg cag ccg gag ctt cag aag ccc ttc aag tac acg      576
Arg Tyr Pro Lys Gly Gln Pro Glu Leu Gln Lys Pro Phe Lys Tyr Thr
            180                 185                 190 acg gtg acc aag agg tcc cgt cgg atc cgg ccc aca cac cct gcc tag      624
Thr Val Thr Lys Arg Ser Arg Arg Ile Arg Pro Thr His Pro Ala
        195                 200                 205

<210> SEQ ID NO 2
<211> LENGTH: 207
<212> TYPE: PRT
<213> ORGANISM: Homo sapiens

<400> SEQUENCE: 2

Met Tyr Ser Ala Pro Ser Ala Cys Thr Cys Leu Cys Leu His Phe Leu
1               5                  10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
 50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160
```

Lys Gly Pro Lys Thr Arg Glu Asn Gln Gln Asp Val His Phe Met Lys
            165                 170                 175

Arg Tyr Pro Lys Gly Gln Pro Glu Leu Gln Lys Pro Phe Lys Tyr Thr
        180                 185                 190

Thr Val Thr Lys Arg Ser Arg Arg Ile Arg Pro Thr His Pro Ala
    195                 200                 205

<210> SEQ ID NO 3
<211> LENGTH: 207
<212> TYPE: PRT
<213> ORGANISM: Mus musculus

<400> SEQUENCE: 3

Met Tyr Ser Ala Pro Ser Ala Cys Thr Cys Leu Cys Leu His Phe Leu
1               5                   10                  15

Leu Leu Cys Phe Gln Val Gln Val Leu Ala Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
            165                 170                 175

Arg Tyr Pro Lys Gly Gln Ala Glu Leu Gln Lys Pro Phe Lys Tyr Thr
        180                 185                 190

Thr Val Thr Lys Arg Ser Arg Arg Ile Arg Pro Thr His Pro Gly
    195                 200                 205

<210> SEQ ID NO 4
<211> LENGTH: 207
<212> TYPE: PRT
<213> ORGANISM: Rattus norvegicus

<400> SEQUENCE: 4

Met Tyr Ser Ala Pro Ser Ala Cys Thr Cys Leu Cys Leu His Phe Leu
1               5                   10                  15

Leu Leu Cys Phe Gln Val Gln Val Leu Ala Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
            85                  90                  95

Val Arg Ile Lys Gly Lys Glu Thr Glu Phe Tyr Leu Cys Met Asn Arg
        100                 105                 110

Lys Gly Lys Leu Val Gly Lys Pro Asp Gly Thr Ser Lys Glu Cys Val
    115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Thr Glu Leu Gln Lys Pro Phe Lys Tyr Thr
            180                 185                 190

Thr Val Thr Lys Arg Ser Arg Arg Ile Arg Pro Thr His Pro Gly
        195                 200                 205

<210> SEQ ID NO 5
<211> LENGTH: 207
<212> TYPE: PRT
<213> ORGANISM: Gallus gallus

<400> SEQUENCE: 5

Met Tyr Ser Leu Leu Ser Ala Cys Thr Cys Leu Cys Leu His Phe Leu
1               5                   10                  15

Leu Leu Cys Phe Gln Val Gln Met Phe Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Lys Gly Glu Asp Gly
65                  70                  75                  80

Asp Lys Tyr Ala Gln Leu Leu Val Glu Thr Asp Thr Phe Gly Ser Gln
            85                  90                  95

Val Arg Ile Lys Gly Lys Glu Thr Asp Phe Tyr Leu Cys Met Asn Arg
        100                 105                 110

Lys Gly Lys Leu Val Gly Lys Pro Asp Gly Thr Ser Lys Glu Cys Val
    115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Val Glu Ile Gln Lys Pro Phe Lys Tyr Thr
            180                 185                 190

Thr Val Thr Lys Arg Thr Lys Arg Ile Arg Pro Thr Asn Pro Ser
        195                 200                 205

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

```
<400> SEQUENCE: 6
ctgaccgaga ggttcaacct gcctctagga                                            30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
ctttatatac acttcgcccg cactttccgc                                            30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
gcgacccaca cgtcaaacta caactccaag                                            30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
cccgttttgg atccgagttt atactgccca                                            30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
acggctgtat gcttcggatc actacaacgc                                            30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
gccattcacc gacacgtacc aaggtctctg                                            30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA
```

```
<400> SEQUENCE: 12
gacacgaggg acagtcttct ggagctctct                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
ccgttcttac tgagggccat gaacataccg                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 14
acctatgcgt ccgcgatcca cagaactgaa                                    30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 15
aagttccggt tgctcggact gcttgaacct                                    30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 16
gcactgagca aatatggacg ggtaaagcgg                                    30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 17
agtcacggga taggagcaga agcgttctct                                    30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 18
```
tggaaatcag gaccgtggca gttggaattg                                        30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
gatttaaggc aacgaacatt tccccctccgc                                       30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 20
atactttggg aagcagagtc cgagttcgcg                                        30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 21
ggtaaaggcc atgtaccagc cctcgtactt                                        30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
taggtgaagt tgggagctat ttcggtgtgc                                        30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
ccctttaaat gatccaagtc cgtgactgcg                                        30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 24
aagctcttgg tcaggacatg gtgtcacagg                                    30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
gtacggacag tcttcattct tggtcccgct                                    30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 26
agctcaaagg catcgtcacc aaactgttct                                    30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 27
gctgtgaaat gtggcgagct gtacaatagc                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 28
tgtgacaagg ttattcagcc agcagggata                                    30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 29
ataaaggctg gctttaaccc cttggatggc                                    30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 30
ggcaatgaac agcgagggat acttgtacac                                    30

```
<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 31
cggattgctg ctgacggtag atcattgatg                                    30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 32
cgggcttttc aatggcaacc tggtggatat                                    30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 33
tacaaccctg tcttcactcc ctggatggca                                    30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 34
tggatccgtt caggatggtg gaggatgtag                                    30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 35
agccactaac acaacagggt ccatgtgaga                                    30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 36
cccgggaggg atacaggact aaacgacacc                                    30
```

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 37
agcggaagag atctctggac atggagggca                                      30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 38
cagtacgtga gggaccaggg cgctatgacc                                      30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 39
ctccacgatg agcttggcga acttgttgcc                                      30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 40
agacgcgggc tcgagatgat gtgagtcgga                                      30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 41
gcccttgatc cggacttgac tcccgaaggt                                      30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 42
agtgtggcag tgggactggt cagtatcaga                                      30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 43
taagtgctac aaaatacctg cgacccgtgt                               30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 44
gagatcaggg aggatggaac agtggtaggc                               30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 45
gggcttcaga ctggtacaca ttgtaaccgt                               30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 46
cgtaggggtg ttctgggtct tctccatgaa                               30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 47
ttcatggaga agacccagaa caccctacg                                30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 48
agccaggacc agctatcacc tacagatcca                               30

<210> SEQ ID NO 49

-continued

```
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 49
gcaattctct gggctgaagt gaagcgatcc                                      30
```